United States Patent [19]

Getman et al.

[11] Patent Number: 4,879,371

[45] Date of Patent: Nov. 7, 1989

[54] SOLID PHASE PEPTIDE SYNTHESIS

[75] Inventors: Daniel P. Getman, St. Louis; Robert M. Heintz, Ballwin, both of Mo.

[73] Assignee: Monsanto Company, St. Louis, Mo.

[21] Appl. No.: 208,942

[22] Filed: Jun. 20, 1988

Related U.S. Application Data

[62] Division of Ser. No. 946,558, Dec. 24, 1986, Pat. No. 4,764,595.

[51] Int. Cl.$^4$ ............................ C07K 1/04; C07K 1/06
[52] U.S. Cl. ..................................... 530/334; 530/325
[58] Field of Search ............................. 530/334, 325; 525/54.11; 526/286, 347.1

[56] References Cited

U.S. PATENT DOCUMENTS

| | | | |
|---|---|---|---|
| 3,995,094 | 11/1976 | Grasby et al. | 526/46 |
| 4,507,230 | 3/1985 | Tam et al. | 530/334 |
| 4,623,484 | 11/1986 | Carpino et al. | 530/334 |
| 4,680,339 | 7/1987 | Fong | 525/54.11 |
| 4,764,594 | 8/1988 | German et al. | 530/334 |
| 4,764,595 | 8/1988 | German et al. | 530/334 |
| 4,801,665 | 1/1989 | German et al. | 325/350 |

OTHER PUBLICATIONS

Samanen et al., "The p-Methylsulfinylbenzyl Groups, A Selectively Clearable Carboxy Protecting Group", 9th American Peptide Symposium in Toronto, pp. 225-228, Jun. 23-28, 1985.

Primary Examiner—Howard E. Schrin
Assistant Examiner—Susan Learned
Attorney, Agent, or Firm—Linda L. Lewis; J. W. Williams, Jr.; Arnold H. Cole

[57] ABSTRACT

A resin and method for using the resin for solid phase peptide synthesis. The resin has a sulfoxide linkage, which is stalbe to strong acid conditions. The sulfoxide linkage can be reduced to a sulfide linkage, which allows cleavage of the peptide from the resin under mild acid conditions.

5 Claims, No Drawings

SOLID PHASE PEPTIDE SYNTHESIS

This is a division of application Ser. No. 946,558, filed Dec. 24, 1986, now U.S. Pat. No. 4,764,595.

FIELD OF THE INVENTION

This invention relates to a resin support for solid phase peptide synthesis and a method of using the resin support to synthesize peptides.

DESCRIPTION OF RELATED ART

The synthesis of peptides is generally carried out through the condensation (or coupling) of the carboxyl group of an amino acid, and the amino group of another amino acid, to form a peptide bond. A sequence can be constructed by repeating the condensation of individual amino acids in stepwise elongation, or, in some cases, by condensation between two preformed peptide fragments (fragment condensation). In both types of condensations, the amino and carboxyl groups that are not to participate in the reaction must be blocked (or protected) with protecting groups. In addition, reactive side chain functionalities of the amino acids also need to be protected.

A successful synthesis of a large peptide by a series of condensation reactions must achieve nearly quantitative recoveries for each chemical step. This requirement has been met by solid-phase peptide synthesis, pioneered by R. B. Merrifield. In such a synthesis, the peptide chain is normally attached by a benzyl-type carboxyl-protecting group to an insoluble polystyrene resin. A first amino acid is attached to the resin through a benzylic ester linkage, is deprotected at its amino site, and coupled with a second amino acid carrying a protected α-amino group, to produce a protected dipeptide ester. The protecting group is removed with trifluoroacetic acid, neutralized to form the free amine with base, and coupled to a second N-protected amino acid. After many repetitions of these steps, the complete peptide is cleaved from the resin with acid treatment. By using the insoluble resin support it is possible to isolate the product of each coupling reaction by filtering the resin and washing it free of by-products and excess starting materials. Barany, G. and Merrifield, R. B., "The Peptides, Vol. 2", Academic Press, Inc., New York, 1979, pp. 1-284; and Kemp-Vellaccio, "Organic Chemistry", pp. 1030-1032 (1980).

In solid phase peptide synthesis, the peptide-resin link is critical to the synthesis procedure. The link must be stable to the deprotection of the amino blocking groups, which typically entails the use of concentrated acid. If the linkage is not stable to deprotecting conditions, the peptide will be prematurely cleaved from the resin. Additionally, the linkage must be readily cleaved upon completion of the synthesis of the peptide, preferably under conditions that will not damage the peptide being recovered.

A number of approaches have been taken to improve the peptide-resin linkage. Merrifield developed a phenylacetamidomethyl linkage which is more stable to the strong acid conditions required to deprotect the amino groups. (Stewart, J. M. and Young, J. D., *Solid Phase Peptide Synthesis*, second edition, Pierce Chemical Co., Rockford, Ill., pp. 11 and 12 and Gross, E. and Meienhofer, J., *The Peptides, Analysis, Synthesis, Biology*, Vol. 2, Academic Press, 1980, pp 3-250).

Because, as peptides become larger and more complex, they are less stable to the acidic condition necessary to deprotect and cleave, researchers developed a peptide resin link that can be cleaved by milder reagents. Wang developed a p-alkoxybenzyl alcohol resin that can be cleaved by 25% trifluoroacetic acid in dichloromethane. Stewart, Id. at 12, 13.

In an attempt to find milder conditions for cleavage, Tam, (U.S. Pat. No. 4,507,230) developed a method of reducing the acidity function of the strong acid used in cleavage, typically anhydrous hydrogen fluoride, by the use of a suitable weak base which would remain largely unprotonated and nucleophilic under the resulting acidic conditions.

None of the above references has disclosed a peptide-resin linkage for solid phase peptide synthesis which affords the combination of acid stability as well as ready cleavage under mild acid conditions.

J. M. Samanen and E. Bradelis disclose in their paper "The p-Methylsulfinylbenzyl Group, A Selectively Cleavable Carboxyl Protecting Group," 9th American Peptide Symposium in Toronto, June 23-28, 1985, a p-methylsulfinylbenzyl group which is useful as a carboxyl protecting group to be used in solution phase peptide synthesis. The sulfoxide substituted benzylic ester linkage is stable to the trifluoracetic acid conditions used to deprotect the amino groups. When the sulfoxide is reduced to a sulfide, the ester group is "unlocked" and is cleavable in anhydrous trifluoroacetic acid. This protecting group has not been disclosed for use in solid phase peptide synthesis.

We have discovered a resin for solid phase peptide synthesis that provides both stability to strong acid conditions and ready cleavage under relatively mild acid conditions to provide a peptide and a resin, and a method for synthesizing a peptide, using such resin.

SUMMARY OF THE INVENTION

The present invention involves a resin for solid phase peptide synthesis and a method for synthesizing a peptide utilizing the resin. The resin comprises the structure

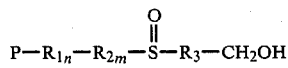

where P is the polymer support, $R_1$ is a substituted or unsubstituted aromatic, $R_2$ is an alkyl having from 1 to 20 carbon atoms, $R_3$ is a substituted or unsubstituted phenyl, and n and m independently equal 1 or 0.

The method of synthesizing a peptide comprising
(a) anchoring protected carboxyl terminal amino acid to a resin of the formula

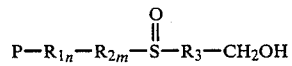

where $R_1$ is a substituted or unsubstituted aromatic, $R_2$ is an alkyl having from 1 to 20 carbon atoms, $R_3$ is a substituted or unsubstituted phenyl and n and m independently equal 0 or 1 to form a benzyl ester linkage;
(b) deprotecting the anchored amino acid;
(c) neutralizing the anchored amino acid to convert to an amine;
(d) coupling a protected carboxyl terminal amino acid to the amine of step (c);

(e) repeating steps (b), (c) and (d) to synthesize the desired peptide on the resin of step (a);
(f) reducing the sulfoxide to a sulfide; and
(g) cleaving the peptide from the resin to obtain the synthesized peptide.

DETAILED DESCRIPTION OF THE INVENTION

THE RESIN

The resin of the present invention has the structure

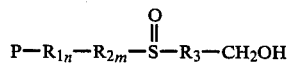

where P is the polymer support, $R_1$ is a substituted or unsubstituted aromatic, preferably an unsubstituted phenyl, and $r_2$ is an alkyl having from 1 to 20 carbon atoms. A preferred alkyl is methylene. $R_3$ is a substituted or unsubstituted phenyl, preferably an unsubstituted phenyl, and n and m independently equal 1 or 0. If $R_1$ and $R_3$ are substituted, the substituent should be such that it will not react under the peptide synthesis conditions. Examples of suitable substituents for $R_1$ and $R_3$ are alkyls, such as methyl or ethyl, aryls such as phenyl, alkenes such as propene, alkynes such as hexyne, nitro groups and halogens such as chloro, fluoro or bromo groups.

The polymer support can be any of a number of polymers, copolymers or combinations of polymers such as polyamide, polysulfamide, substituted polyethylenes, polyethyleneglycol, phenolic resins, polysaharides, or polystyrene. The polymer support can also be any solid that is unsoluble and inert to solvents used in peptide synthesis, such as glass beads. The preferred polymer support is a gel prepared by suspension copolymerization of styrene and about one percent of m-divinylbenzene or crosslinking agent. Such crosslinked gels swell in organic solvents to about 5 to 6 times their dry volume. The swelling allows solvents and reactants access to the reaction sites on the polymer and allows reaction in the interior of the polymer as well as the exterior surface.

Functional groups can be introduced into the polymer by chloromethylation which can be accomplished by using chloromethyl methyl ether. The chloromethylated crosslinked polystyrene gel is referred to in the art as the Merrifield resin. The Merrifield resin is described in further detail in Stewart, J. M. and Young, J. D. *Solid Phase Peptide Synthesis*, second edition, Pierce Chemical Co., Rockford, Illinois which is hereby incorporated by reference The preferred resin is of the formula

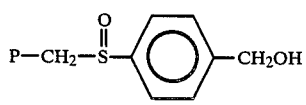

Resin I where P is a crosslinked polystyrene resin.

A second preferred resin can also be of the formula

Resin II where $R_1$ is an alkyl having from 1 to 20 carbon atoms, P is the polymer support and n is 0 to 20. The synthesis of Resin I, which is disclosed in detail in copending application, Ser. No. 947,651 which is hereby incorporated by reference, is effected by reacting a polymer support, P, with a mercaptan of the formula

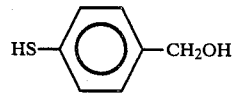

to form a sulfide resin and oxidizing the resin to form a sulfoxide resin. The synthesis of Resin II, which is disclosed in detail in copending application Ser. No. 031,823, which is hereby incorporated by reference, is effected by reacting (halomethyl)phenyl alkylcarboxylic acid halide and an acid protecting group to form an ester, reacting the ester with p-mercaptobenzyl alcohol to form a sulfide, oxidizing the sulfide to form a sulfoxide, reacting a carboxyl terminal N-blocked amino acid with the alcohol group of the sulfoxide to form an ester, hydrolysing the acid protecting group from the ester of the sulfoxide to form the acid and anchoring the sulfoxide via the acid group to a functionalized polymer to form a resin for solid phase peptide synthesis.

THE PEPTIDE SYNTHESIS

The peptide synthesis is summarized below:

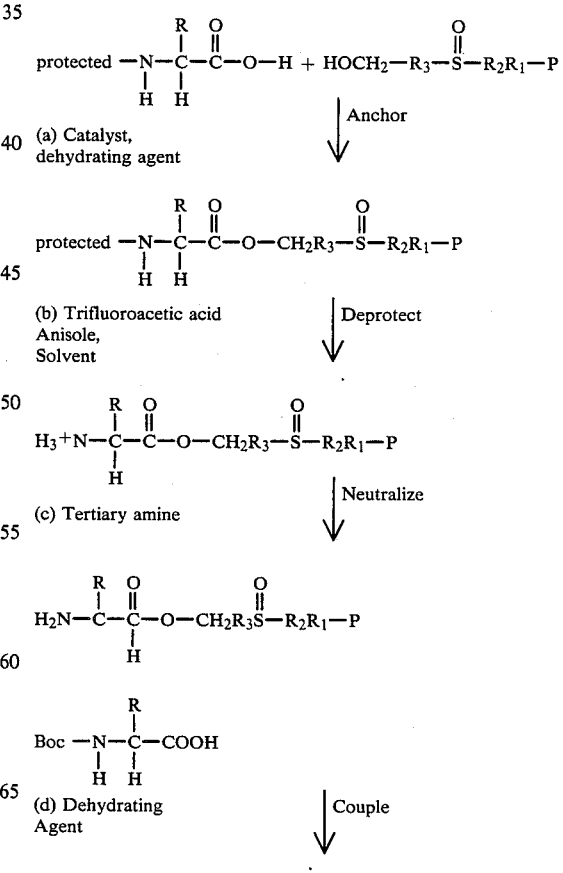

-continued

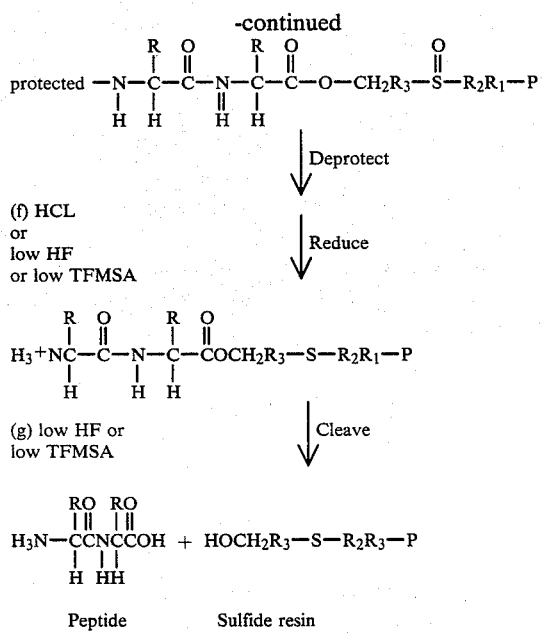

(f) HCl
or
low HF
or low TFMSA

↓ Deprotect

↓ Reduce

H₃⁺NC—C—N—C—COCH₂R₃—S—R₂R₁—P (with R, O, H substituents)

(g) low HF or
low TFMSA

↓ Cleave

H₃N—CCNCCOH + HOCH₂R₃—S—R₂R₃—P

Peptide          Sulfide resin

The peptide synthesis steps involving anchoring, deprotecting, neutralizing and coupling are well known in the art and are disclosed in detail by Steward et al., supra, and described in detail hereinafter.

The amino acid to be anchored to the resin is a carboxyl terminal amino acid wherein the amino end is blocked by a protecting group. Suitable protecting groups include 9-fluorenyl-methyloxycarbonyl (Fmoc), 2-(4-biphenylyl)-propyl(2)oxycarbonyl(Bpoc), 2-phenylpropyl(2)-oxycarbonyl (Poc) and t-butyloxycarbonyl (Boc), etc. Side-chain functional groups must also be blocked with protecting groups such as benzyl-based derivatives. The carbonyl group of the amino acid is attached to the resin by a benzylic ester linkage. Any suitable condensation reaction can be used to anchor the amino acid to the resin. In the preferred reaction to attach the resin, the resin is suspended in a solvent which swells the resin, such as methylene chloride, tetrahydrofuran, benzene, toluene or N,N-dimethylformamide. The blocked amino acid, a catalyst such as N,N-dimethyl-4-aminopyridine, and a coupling agent such as 1,3-diisopropylcarbodiimide or 1,3-dicyclohexylcarbodiimide are mixed at room temperature.

The amino acid anchored to the resin can be deprotected by any method known in the art, such as acidolysis. When the resin is in the sulfoxide state the resin is stable to deprotecting conditions. The preferred method is to deprotect by reacting with trifluoroacetic acid, a carbonium ion scavenger such as anisole, dimethyl sulfide, resorcinol or methionine, the preferred scavenger being anisole and a solvent such as methylene chloride to form an amine salt. The deprotected amino acid is then neutralized by treating with a tertiary amine such as diisopropylethylamine, triethylamine or trimethylamine to form the free amine.

As described hereinafter, the resin can be produced by first forming a sulfide linkage and oxidizing a sulfide linkage under suitable conditions to be desired sulfoxide linkage.

The deprotecting step also "caps" any residual sulfide resin left when the sulfide is oxidized to form the sulfoxide in the resin synthesis as follows:

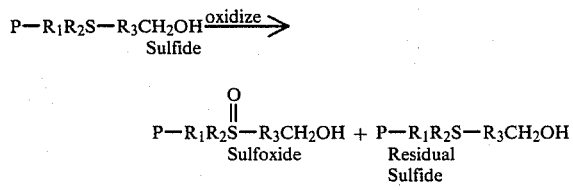

O
‖
P—R₁R₂S—R₃CH₂OH + P—R₁R₂S—R₃CH₂OH
Sulfoxide            Residual
                     Sulfide The residual sulfide resin reacts with the carboxyl terminal amino acid in the first coupling step but is not stable to the acid treatment of the deprotecting step, thereby leading to premature cleavage of the desired peptide being synthesized. By capping the residual sulfide resin, this premature cleavage is stopped after the first amino acid and the overall yield of the peptide is increased. The anchored sulfide resin is capped in the deprotecting step.

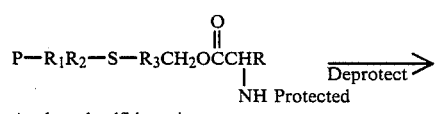

Anchored sulfide resin

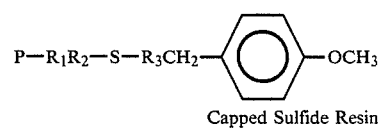

Capped Sulfide Resin

Another blocked carboxyl terminal amino acid is coupled with the free amine by reacting in the presence of a coupling agent and a protected-amino acid. The deprotecting, neutralizing and coupling steps are repeated until the desired peptide is synthesized.

Whereas the sulfoxide linkage is stable to the trifluoroacetic acid condition used to deprotect the amino acid, the sulfide linkage can be cleaved by anhydrous trifluoroacetic acid. There are many ways to accomplish the reduction (see *Advanced Organic Chemistry,* 2nd edition, J. March, 1977, p. 1130, which is hereby incorporated by reference). A preferred method involves treating the resin with a strong acid such as anhydrous hydrochloric acid and in a separate step cleave the peptide from the resin using a strong acid such as hydrofluoric acid, trifluoroacetic acid, hydrobromic acid, or trifluoromethanesulfonic acid in the presence of a suitable carbonium ion scavenger such as stated above. Another preferred method involves simultaneously reducing the sulfoxide to a sulfide and cleaving by treating with hydrofluoric acid (HF) or trifluoromethanesulfonic acid (TFMSA) in the presence of a nucleophilic scavenger under $S_N2$ conditions as described by Tam et al., U.S. Pat. No. 4,507,230, and Tam et al., JACS, 1986, 108, 5242–5251, which are hereby incorporated by reference.

The following examples are for illustration purposes only and are not intended to limit the scope of this invention.

EXAMPLES

The resin used in the following peptide synthesis was prepared as follows:

Step 1

Attachment of Sulfoxide Linker to Resin

A crosslinked polystyrene support was functionalized as follows:

In a 500 ml round-bottom flask were placed 20.00 g of a chloromethylated 1% cross-linked polystyrene; (Merrifield resin) 200–400 mesh, 1.1 meq chloride/gram, 22 mmol; 160 ml of dry tetrahydrofuran (THF); 6.32 g (45 mmol) of 4-mercaptobenzyl alcohol and 6.6 ml (4.8 g, 48 mmol) of triethylamine. The flask was placed on a rotary evaporator equipped with a condenser which allowed reflux of solvent into the flask, placed under a nitrogen atmosphere and immersed in a water bath at 60° C. The flask was rotated for 24 hours. After cooling to room temperature, the resin was transferred to a shaker vessel equipped with a coarse glass frit for filtering and washed successively three times with 160 ml each of THF, 20% water/80% THF (v:v), 50% water/ 50% methanol and methanol. The resin was dried under vacuum. The resin was submitted for elemental analysis and found to contain 0.44 weight percent chloride (0.12 meq/g) and 2.43 weight percent sulfur (0.79 meq/gram). Infrared analysis of this resin showed only a trace of the band at 1265 cm$^{-1}$ due to the chloromethyl group, indicating almost complete reaction of the chloromethyl with the mercaptan.

The functionalized resin was oxidized from a sulfide to a sulfoxide as follows:

In a 500 ml round-bottom flask were placed 17.1 g (.79 meq sulfur/g, 13.5 mmol) of the above functionalized resin and 170 ml methylene chloride. After cooling to 5° C., 2.47 g of 83.3% meta-chloroperbenzoic acid oxidizing agent (2.06 g active peracid, 11.9 mmol) was slowly added over a fifteen minute period. After the addition, the flask was rotated on a rotary evaporator in a cold room at 7° C. for 24 hours. The resin was transferred to a shaker vessel and washed successively three times each with 150 ml of methylene chloride and methanol.

Infrared analysis of this group showed a strong band at 1020 cm$^{-1}$ due to the sulfoxide group.

EXAMPLE 1

Step 2

Anchoring the First Amino Acid

The first amino acid was anchored to sulfoxide resin as follows:

In a shaker vessel was placed 4.00 g (0.79 meq sulfur/g, 3.16 mmol) of sulfoxide resin and 40 ml methylene chloride. The following reagents were added, in order, with a 1 minute shake between additions; 2.10 g (7.9 mmol) of N-(tert-butyloxycarbonyl)-L-phenylalanine, 40 mg (0.33 mmol) of N,N-dimethyl-4-aminopyridine and 1.5 ml (1.37 g, 10.9 mmol) of 1,3-diisopropylcarbodiimide. The reaction mixture was shaken at room temperature for 24 hours, the solvent drained and the resin washed successively three times each with 40 ml methylene chloride, methanol and methylene chloride. To the wet resin was added 40 ml methylene chloride, 3.2 ml (2.43 g, 18.8 mmol) N,N-diisopropylethylamine and 1.5 ml (1.80 g, 17.7 mmol) acetic anhydride, and the vessel was shaken for 2 hours. After draining the solvent, the resin was washed three times with 40 ml methylene chloride and methanol, and dried under vacuum.

Amino acid analysis of this resin showed a phenylalanine loading of 0.64 meq/g of resin.

Step 1

Deprotecting the Sulfoxide Resin and Capping the Residual Sulfide Resin

The resin was deprotected and residual sulfide resin was capped as follows:

In order to remove any phenylalanine attached to a sulfide linker group and at the same time cap these groups, the above resin was treated with 40 ml of 45% trifluoroacetic acid/5% anisole/50% methylene chloride (v:v:v) for 21 hours, washed three times with 40 ml each of methylene chloride and methanol, and dried under vacuum. Amino acid analysis of this resin showed a phenylalanine loading of 0.58 meq/g of resin. This resin has only phenylalanine attached to a sulfoxide linker group, (the sulfide linker groups have been capped) and is now ready for use in peptide synthesis.

Step 4

Reducing the Sulfoxide Linkage and Cleavage

The sulfoxide linkage was reduced to a sulfide linkage and the amino acid was cleaved from the resin under low HF conditions as follows:

A sample of the above phenylalanine-substituted sulfoxide resin (0.50 g, 0.58 meq/g, 0.29 mmol) was treated with a mixture of 1.0 ml p-cresol, 6.5 ml dimethyl sulfide and 2.5 ml anhydrous hydrogen fluoride for 2 hours at 0° C. After stripping the reagents under vacuum, the resin was successively washed twice with 5 ml each of methylene chloride, trifluoroacetic acid, methylene chloride and methanol and then dried under vacuum. Amino acid analysis of the resin showed a phenylalanine content of 0.062 meq/g, indicating that an 89% cleavage yield had occurred. Infrared analysis showed no sulfoxide band at 1020 cm$^{-1}$, indicating that the sulfoxide group had been fully reduced.

In an alternative method of reducing the sulfoxide linkage and cleaving the amino acid from the resin, low trifluoromethanesulfonic acid conditions were used as follows:

A sample of phenylalanine-substituted sulfoxide resin from above (0.20 g, 0.58 meq/g, 0.12 mmol) was treated with a mixture of 0.60 ml dimethyl sulfide, 1.2 ml trifluoroacetic acid and 0.20 ml trifluoromethanesulfonic acid at room temperature for 1 hour. The resin was washed three times successively with 5 ml each of trifluoroacetic acid, methylene chloride and methanol, then dried under vacuum. Amino acid analysis of the resin showed a phenylalanine content of 0.055 meq/g, indicating a 91% cleavage yield had occurred. Infrared analysis for the presence of the sulfoxide group was complicated by bands which were attributed to trifluoromethanesulfonic acid.

EXAMPLE 2

A dipeptide of L-leucine and L-phenylalanine was prepared using the above described resin. N-(tert-butyloxycarbonyl)-L-leucine was coupled using the procedure of Example 1. Amino acid analysis of this resin showed a leucine content of 0.75 meq/g. When treated with 45% trifluoroacetic acid to deprotect and cap the residual sulfide as in Example 1, the leucine content dropped to 0.49 meq/g. A sample of this resin (0.994 g, 0.49 mmol) was washed twice with a solution of 10% diisopropyl ethylamine in methylene chloride, followed by three washes with methylene chloride to neutralize the resin. The resin was coupled with N(tert-butyloxycarbonyl)-L-phenylalanine by suspending the resin in 10 ml methylene chloride and adding 464 mg (1.75 mmol) N-(tert-butyloxycarbonyl)-L-phenylalanine and 0.27 ml (235 mg, 1.86 mmol) N,N-diisopropylcarbodiimide. After shaking for two hours, the resin was washed three times with methylene chloride and dried under vacuum. Amino acid analysis showed the leucine content to be 0.40 meq/g and the phenylalanine content to be 0.40 meq/g.

The sulfoxide resin was deprotected and reduced the sulfide by anhydrous hydrogen chloride and the peptide was cleaved from the resin by trifluoroacetic acid as follows:

A sample of the above coupled resin from Example 2 (100 mg, 0.04 mmol) was shaken for four hours with 5 ml of a 4.1 molar solution of anhydrous hydrogen chloride in dioxane. The resin was washed five times with 5 ml methylene chloride and dried under vacuum. Amino acid analysis showed the following amino acid content: leucine (0.28 meq/g) and phenylalanine (0.32 meq/g), indicating that a 25% cleavage had occurred. The resin was then treated with 5 ml of 45% trifluoroacetic acid/5% anisole/50% methylene chloride (v:v:v) for twenty-four hours, filtered, washed six times with 5 ml methylene chloride and dried under vacuum. Amino acid analysis of this resin showed the following amino acid content: leucine (0.08 meq/g) and phenylalanine (0.11 meq/g), indicating a 72-81% cleavage had occurred.

In a separate experiment, when the treatment with anhydrous hydrogen chloride was extended to twenty-four hours and the trifluoroacetic acid treatment maintained at twenty-four hours, no change in the amount of cleavage was observed.

EXAMPLE 3

Preparation of 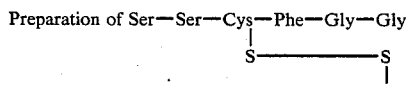

To a 4.00 g sample of a sulfoxide resin, prepared according to Step 1, was attached N-(t-butyloxycarbonyl)-0-2, 6-dichlorobenzyl-L-tyrosine following the procedure of Step 2. Amino acid analysis of the resin before and after treatment with trifluoroacetic acid showed loadings of 0.51 meq/g and 0.42 meq/g, respectively. To the resin were then coupled the above listed N-Boc-L-amino acids using 1-hydroxybenzotriazole (HOBT)/N,N-diisopropylcarbodiimide (DIPCD) couplings using five equivalents of reagent (amino acid/DIPCD/HOBT = 1.0/1.2/2.0, respectively) in 50:50 (v:v) methylene chloride/N,N-dimethylformamide as the solvent. The protecting groups used for the various N-Boc-L-amino acids were as follows; serine (O-benzyl), cysteine-19 (S-para-thiomethylbenzyl), cysteine-3 (S-para-methoxybenzyl), arginine (Ng-2,4,6-Trimethylbenzenesulfonyl), aspartic acid (O-benzyl) and tyrosine (O-2,6-dichlorobenzyl). The amino acids were deprotected using 45% trifluoroacetic acid/5% anisole/50% methylene chloride. After the peptide was synthesized, amino acid analysis of the resin gave the following results; Asp (0.38 meq/g), Ser (0.40), Gln (0.19), Gly (0.86), Ala (0.20), Ile (0.32), Leu (0.20), Tyr (0.18), Phe (0.19) and Arg (0.51), consistent with a successful synthesis. A sample of this resin (0.15 g) was reduced from sulfoxide to sulfide and cleaved using dimethyl sulfide/p-cresol/anhydrous hydrogen fluoride (6.5 mL/1.0 mL/2.5 mL, respectively) for two hours at 0° C., followed by removal of volatiles under vacuum and addition of anhydrous hydrogen fluoride (10 mL) for one hour at 0° C. according to the procedure of Tam et al, *J. Amer. Chem. Soc.*, 1983, 105, 6442-6455, which is hereby incorporated by reference. Amino acid analysis of the resin following cleavage indicated that a 73% cleavage had occurred. The crude material was cyclized by dissolving in water, raising the pH to 8.5 and allowing to stand overnight in an open beaker. The crude material was purified by preparative HPLC on a Vydac C-18 column. The material was sequenced and shown to have the correct structure for the desired peptide.

EXAMPLE 4

Preparation of 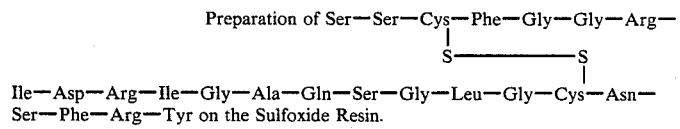

To a 3.00g sample of sulfoxide resin, prepared according to Step 1, was attached N-(t-butyloxycarbonyl)-0-(2-bromobenzyloxycarbonyl)-L-tyrosine following the procedure of Step 2. Amino acid analysis of the resin before and after treatment with trifluoroacetic acid showed loadings of 0.59 meq/g and 0.40 meq/g, respectively. To the resulting resin was then sequentially coupled Nα-(t-butyloxycarbonyl)-Ng-(para-tolylsulfonyl)-L-arginine and N-(t-butyloxycarbonyl)-L-phenylalanine utilizing five equivalents of 1-hydroxybenzotriazole (HOBT)/diisopropylcarbodiimide (DIPCD) couplings (amino acid/DIPCD/HOBT = 1.0/1.2/2.0, respectively) in 50:50 (v:v) methylene chloride/N,N-dimethylformamide as solvent. The amino acids were deprotected with 45% trifluoroacetic acid/5% anisole/50% CH2Cl2. Amino acid analysis of this resin showed the following loadings; Tyr (0.40 meq/g), Arg (0.36 meq/g) and Phe (0.42 meq/g). A sample of this resin (0.94g, 0.38 mmol) was placed in an Applied Biosystems Automated Peptide Synthesizer Model 430A and subjected to standard peptide synthesis conditions (four equivalents of amino acid, N,N-dicyclohexylcarbodiimide, 90:10 v:v methylene chloride/N,N-dimethylformamide, 0.5 hour couplings). The arginine and asparagine amino acids were double-coupled using HOBT. The deprotecting groups used for the various N-Boc-L-amino acids were as follows; serine (0-benzyl)cysteine(S-acetamidomethyl), arginine (Ng-para-tolylsulfonyl), aspartic acid (0-benzyl) and tyrosine (0-2-bromobenzyloxycarbonyl). After the synthesis was completed, the resin obtained gave the following amino acid analysis Asp (0.36 meq/g), Ser (0.36), Gln (0.16), Gly (0.75), Ala (0.16), Ile (0.25), Leu (0.17), Tyr (0.19), Phe (0.35) and Arg (0.50), consistent with a successful synthesis. The sulfoxide linkage was reduced to sulfide and cleaved using dimethyl sulfide/p-cresol/anhydrous hydrogen fluoride (6.5mL/1.0mL/2.5mL, respectively) for two hours at 0° C., followed by removal of volatiles under vacuum and addition of anhydrous hydrogen fluoride (10 mL) for one hour at 0° C., according to the procedure of Tam et al, supra. In this manner 930 mg of crude peptidic material was obtained, a portion of which was purified by preparative HPLC on a Waters Bondapak C-18 Column (19 mm×150 mm), cyclized in acetic acid with a saturated iodine/water solution and purified by preparative HPLC. Amino acid analysis of the resin following the cleavage indicated that a 76% yield of peptide was obtained. Amino acid analysis of the purified peptide gave the following results; Asp (2.13), Ser (3.62), Gln (1.07), Gly (5.14), Ala (1.06), Ile (1.82), Leu (1.05), Tyr (0.97), Phe (2.04) and Arg (3.11).

EXAMPLE 5

Preparation of Ser—Ser—Cys—Phe—Gly—Gly—Arg—
              |
              S————————S
                       |
Ile—Asp—Arg—Ile—Gly—Ala—Gln—Ser—Gly—Leu—Gly—Cys—Asn—
Ser—Phe—Arg—Tyr on the Sulfoxide Resin.

To a 2.00g sample of sulfoxide resin, prepared according to Step 1, was attached N-(t-butyloxy-carbonyl)-0-(2-bromobenzyloxycarbonyl)-L-tyrosine following the procedure of Step 2. Amino acid analysis of the resin before and after treatment with trifluoroacetic acid showed loadings of 0.51 meq/g and 0.39 meq/g, respectively. To the resulting resin was then sequentially coupled Nα-(t-butyloxycarbonyl)-Ng-(2,4,6-trimethylbenzenesulfonyl)-L-arginine and N-(t-butyloxycarbonyl)-L-phenylalanine utilizing 2.5 equivalents of HOBT/DIPCD couplings (amino acid/DIPCD/HOBT=1.0/1.2/2.0, respectively) in 50:50 (v:v) methylene chloride/N,N-dimethylformamide as the solvent. The amino acid was deprotected with 45% trifluoroacetic acid/5% anisole/50% methylene chloride. Amino acid analysis of this resin showed the following loadings; Tyr (0.30 meq/g), Arg (0.21 meq/g) and Phe (0.32 meq/g). A sample of this resin (0.94g, 0.28 mmol) was then placed in an Applied Biosystems Automated Peptide Synthesizer Model 430A and subjected to standard peptide synthesis conditions (four equivalents of amino acid, N,N-dicyclohexylcarbodiimide, 90:10 (v:v) methylene chloride/N,N-dimethylformamide, 0.5 hour couplings). The arginine and asparagine amino acids were double-coupled using HOBT. The protecting groups for the various N-Boc-L-amino acids were as follows; serine (0-benzyl), cysteine (S-acetamidomethyl), arginine (Ng-2,4,6-trimethylbenzenesulfonyl), aspartic acid (0-benzyl) and tyrosine (0-2-bromobenzyloxycarbonyl). After the synthesis was completed the resin obtained gave the following amino acid analysis; Asp (0.30 meq/g), Ser (0.32), Gln (0.13), Gly (0.65), Ala (0.12), Ile (0.20), Leu (0.13), Tyr (0.14), Phe (0.30) and Arg (0.36), consistent with a successful synthesis.

The sulfoxide linkage of a sample of this resin (0.50g) was reduced to sulfide linkage and cleaved using a mixture of dimethylsulfide/trifluoroacetic acid/m-cresol/-trifluoromethanesulfonic acid (3.0 mL/5.0mL/1.0mL/1.0mL, respectively) according to the procedure of Tam et al., *J. Amer. Chem. Soc.*, 1986, 108, 5242–5251, which is hereby incorporated by reference, except that the cleavage was run at room temperature for five hours, to afford 334 mg of crude peptidic material The peptide was dissolved in 30 mL of an 80:20 (v:v) mixture of acetic acid/water and 10 mL of a saturated iodine in acetic acid solution was added. After stirring at room temperature for one hour, a weakly basic resin available from Dow, under the trade designation Dowex ® (Sigma WGR2) was added and stirring continued for an additional one hour. The resin was filtered, washed with water and the filtrate concentrate under reduced pressure. Chromatography on a Waters Bondapak ® C-18 preparative column (19 mm×150 mm) afforded pure peptide which was sequenced and shown to have the correct structure. Amino acid analysis of the resin following the cleavage indicated that a 72% cleavage had occurred.

What is claimed is:

1. A method of synthesizing a peptide comprising
   (a) anchoring protected carboxyl terminal amino acid to a resin of the formula

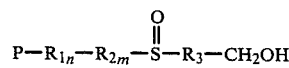

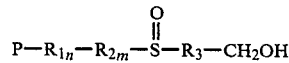

where $R_1$ is a substituted or unsubstituted aromatic, $R_2$ is an alkyl having from 1 to 20 carbon atoms, $R_3$ is a substituted or unsubstituted phenyl and n and m independently equal 0 or 1 to form a benzyl ester linkage;
   (b) deprotecting the anchored amino acid;
   (c) neutralizing the anchored amino acid to convert to an amine;
   (d) coupling a protected carboxyl terminal amino acid to the amine of step (c);
   (e) repeating steps (b), (c) and (d) to synthesize the desired peptide on the resin of step (a);
   (f) reducing the sulfoxide to a sulfide; and
   (g) cleaving the peptide from the resin to obtain the synthesized peptide.

2. The method of claim 1 wherein the sulfoxide linkage is reduced to a sulfide linkage by treating with hydrochloric acid, and the peptide is cleaved by treating with an acid selected from the group consisting of trifluoroacetic acid, hydrobromic acid, hydrofluoro acid and trifluoromethanesulfonic acid in the presence of a carbonium ion scavenger.

3. The method of claim 1 wherein the sulfoxide linkage is reduced to a sulfide linkage and the peptide cleaved simultaneously by treating with low hydrofluoric acid or low trifluoromethanesulfonic acid in the presence of base under $S_N2$ conditions.

4. The method of claim 1 wherein a residual sulfide resin is capped in the deprotecting step.

5. The method of claim 4 wherein the deprotecting step is effected by reacting the blocked amino acid with trifluoroacetic acid in the presence of carbonium ion scavengers.

* * * * *